United States Patent [19]

Bhatt et al.

[11] Patent Number: 4,728,609

[45] Date of Patent: Mar. 1, 1988

[54] RECOMBINANT GROWTH HORMONE RELEASING FACTOR

[75] Inventors: Ram S. Bhatt, Nutley; Kenneth J. Collier, Rockaway; Robert M. Crowl, Little Falls; Mohindar S. Poonian, West Caldwell, all of N.J.

[73] Assignee: Hoffmann-La-Roche Inc., Nutley, N.J.

[21] Appl. No.: 778,779

[22] Filed: Sep. 24, 1985

Related U.S. Application Data

[63] Continuation of Ser. No. 456,660, Jan. 10, 1983, abandoned, and a continuation-in-part of Ser. No. 439,168, Nov. 4, 1982, abandoned.

[51] Int. Cl.[4] .................. C12P 21/00; C12P 21/02; C12N 15/00; C12N 1/20; C12N 1/00; C07H 15/12

[52] U.S. Cl. .................................. 435/68; 435/70; 435/172.3; 435/253; 435/320; 935/13; 536/27

[58] Field of Search .................. 435/172.3, 68–70, 435/253, 317; 935/13; 536/27

[56] References Cited

U.S. PATENT DOCUMENTS

4,293,652 10/1981 Cohen ........................... 435/172.3
4,353,989 10/1982 Bender et al. ................. 435/172.3
4,356,270 10/1982 Itakura et al. ................. 435/317

OTHER PUBLICATIONS

Brazeau et al, PNAS USA vol. 79, pp. 7909–7913, Dec. 1982.
Spiess et al, Biochemistry vol. 21, pp. 6037–6040 (1982).
Rivier et al, Nature, vol. 300, pp. 276–278 Nov. 18, 1982.
Woods et al, PNAS USA vol. 79, pp. 5661–5665 Sep. 1982.
Guillemain et al, Science vol. 218, pp. 585–587, Nov. 5, 1982.
Nair et al, Endocrinology vol. 103, pp. 112–120, 1978.
Guarente et al, Science vol. 209, pp. 1428–1430, Sep. 19, 1980.
Taniguchi et al, PNAS vol. 77, pp. 5230–5233, Sep. 1980.
Derynck et al, Nature vol. 287, pp. 193–197, Sep. 18, 1980.
Mercereau-Puijalon et al, Nature vol. 275, pp. 505–510, Oct. 12, 1978.
Helling et al, Genetic Engineering Ed. by Chakrabartz CRC Press pp. 1–30, 1978.

*Primary Examiner*—Alvin E. Tanenholtz
*Attorney, Agent, or Firm*—Jon S. Saxe; George M. Gould; Julie M. Prlina

[57] ABSTRACT

Th preparation of a double-stranded polydeoxy ribonucleotide having cohesive termini each comprising one strand of a double-strand restriction endonuclease recognition site and, between the termini, a structural gene coating for the expression of recombinant growth hormone releasing factor, at least a majority of the codons and the coding strand of said gene being codons preferred for the expression of microbial genomes; a method of producing such DNA a recombinant microbial cloning vehicle comprising such DNA and the novel methods of producing said peptide are described.

27 Claims, 15 Drawing Figures

THE TRANSLATED SEQUENCE IS:

```
                    22                         37                         52
ATG TAT GCT GAC GCG ATC TTC ACT AAC TCT TAC CGT AAG GTC CTC GGT CAA
MET TYR ALA ASP ALA ILE PHE THR AEN SER TYR ARG LYS VAL LEU GLY GLN 67                         82                         97              112
CTT TCC GCC AGG AAG TTG CTG CAG GAT ATT ATG TCT AGA CAA CAA GGC GAA TCC
LEU SER ALA ARG LYS LEU LEU GLN ASP ILE MET SER ARG GLN GLN GLY GLU SER 127                        142
AAC CAA GAG CGT GGT GCT CGA GCT CGT TTG TAA GTC GAC G
ASN GLN GLU ARG GLY ALA ARG ALA ARG LEU
```

THE NUCLEOTIDE SEQUENCE IS:

```
         10         20         30         40         50
   AATTCTATG TATGCTGACG CGATCTTCAC TAACTCTTAC CGTAAGGTCC
         GATAC ATACGACTGC GCTAGAAGTG ATTGAGAATG GCATTCCAGG 60         70         80         90        100
   TCGGTCAACT TTCCGCCAGG AAGTTGCTGC AGGATATTAT GTCTAGACAA
   AGCCAGTTGA AAGGCGGTCC TTCAACGACG TCCTATAATA CAGATCTGTT 110        120        130        140        150
   CAAGGCGAAT CCAACCAAGA GCGTGGTGCT CGAGCTCGTT TGTAAGTCGA
   GTTCCGCTTA GGTTGGTTCT CGCACCACGA GCTCGAGCAA ACATTCAGCT

CG
   GCTTAA
```

Figure 2

THE TRANSLATED SEQUENCE IS:

```
                          22                              37                           52
ATG TAT GCT GAC GCG ATC TTC ACT AAC TCT TAC CGT AAG GTC CTC GGT CAA
MET TYR ALA ASP ALA ILE PHE THR AEN SER TYR ARG LYS VAL LEU GLY GLN 67                            82                         97                        112
CTT TCC GCC AGG AAG TTG CTG CAG GAT ATT ATG TCT AGA CAA CAA GGC GAA TCC
LEU SER ALA ARG LYS LEU LEU GLN ASP ILE MET SER ARG GLN GLN GLY GLU SER 127                       142
AAC CAA GAG CGT GGT GCT CGA GCT CGT TTG TAA GTC GAC G
ASN GLN GLU ARG GLY ALA ARG ALA ARG LEU
```

THE NUCLEOTIDE SEQUENCE IS:

```
        10         20         30         40         50
AATTCTATG  TATGCTGACG CGATCTTCAC TAACTCTTAC CGTAAGGTCC
    GATAC  ATACGACTGC GCTAGAAGTG ATTGAGAATG GCATTCCAGG 60         70         80         90        100
TCGGTCAACT TTCCGCCAGG AAGTTGCTGC AGGATATTAT GTCTAGACAA
AGCCAGTTGA AAGGCGGTCC TTCAACGACG TCCTATAATA CAGATCTGTT 110        120        130        140        150
CAAGGCGAAT CCAACCAAGA GCGTGGTGCT CGAGCTCGTT TGTAAGTCGA
GTTCCGCTTA GGTTGGTTCT CGCACCACGA GCTCGAGCAA ACATTCAGCT

CG
GCTTAA
```

Figure 3

ARROWS MARK RECOGNITION SITES NOT CUTTING SITES.

```
         10        20        30        40        50        60        70
GAATTCTATGTATGCTGACGCGATCTTCACTAACTCTTACCGTAAGGTCCTCGGTCAACTTTCCGCCAGG
^             ^^  ^^                       ^  ^       ^              ^
EcoRI         DFNI                         AEuI  HINDII              ECORII
EcoRI         FNuDII                       AvaII
       HGAI MBDI                             MNLI
            MBDII 80        90       100       110       120       130       140
AAGTTGCTGCAGGATATTATGTCTAGACAACAAGGCGAATCCAACCAAGAGCGTGGTGCTCGAGCTCGTT
  ^^^               ^           ^^^                     ^   ^^^ ^^
  BBVI              XBAI        EcoRI•                  HGIAI   ALUI
  FNU4HI                        HINFI                   AVAI
    PSTI                        HINFIII                    HGIAI
                                                           HGIJII
                                                            SACI
                                                            TAQI
                                                            XHDI

150
TGTAAGTCGACGAATTC
   ^^^   ^^
   ACCI   ECORI
   SALI   ECORI•
   HINDII
        HINFIII
     TAQI
```

Figure 4

GRF-OH(44) Gene Synthesis

| Fragment # | 5'- Sequence -3' | |
|---|---|---|
| 1 | AATTCTATGTATGCTGA | (2-18) |
| 2 | ATCGCGTCAGCATACATAG | (134-152') |
| 3 | CGCGATCTTCACTAACT | (19-35) |
| 4 | GGTAAGAGTTAGTGAAG | (117-133') |
| 5 | CTTACCGTAAGGTCCT | (36-51) |
| 6 | TGACCGAGGACCTTAC | (101-116') |
| 7 | CGGTCAACTTTCCGCC | (52-67) |
| 8 | GCAACTTCCTGGCGGAAAGT | (81-100') |
| 9 | AGGAAGTTGCTGCA | (68-81) |
| 10 | GACATAATATCCTGCA | (65-80') |
| 11 | GGATATTATGTCTAGACAA | (82-100) |
| 12 | ATTCGCCTTGTTGTCTA | (48-64') |
| 13 | CAAGGCGAATCCAACCA | (101-117) |
| 14 | CACGCTCTTGGTTGG | (33-47') |
| 15 | AGAGCGTGGTGCTCGA | (118-133) |
| 16 | ACGAGCTCGAGCAC | (19-32') |
| 17 | GCTCGTTTGTAAGTCGACG | (134-152) |
| 18 | AATTCGTCGACTTACAA | (2-18') |

FRAGMENT C (x 2) = 140 bp

Solid Support Phosphite Methodology

Loading of the Support $\hat{B}$ = Protected base

DMTr = Dimethoxytrityl

Deprotection and Release of Oligonucleotides from the Support

Figure II 1
2

B = Thymine (T)
    N-benzoyladenine ($A^{Bz}$)
    N-anisoylcytidine ($C^{An}$)
    N-isobutyrylguanine ($G^{ibu}$)
DMT = Dimethoxytrityl

Figure 13

14'  TACTCTTGGTTGG
15'  AGAGTAAGTCGACG
16'  AATTCGTCGACT

```
                    15'
              AGAGTAAGTCGACG
      GGTTGGTTCTCAT TCAGCTGGTTAA
           14'       ↑      16'
```

14"      CCACGCTCTTGGTTGG
15"      AGAGCGTGGTGCTTAAGTCGACG
16"      AATTCGTCGACTTAAGCA

15"
         AGAGCGTGGTGCTTAAGTCGACG
GGTTGGTTCTCGCACC ACGAATTCAGCTGCTTAA
         14"                    16"

RECOMBINANT GROWTH HORMONE RELEASING FACTOR

RELATED APPLICATION

This is a continuation of application Ser. No. 456,660 filed Jan. 10, 1983, now abandoned and a continuation-in-part of copending U.S. patent application Ser. No. 439,168 filed Nov. 4, 1982 (abandoned).

BACKGROUND OF THE INVENTION

Dr. Guillemin and coworkers at the Salk Institute have recently (Science, 218, 585-587 (Nov. 5, 1982), see also New York Times, Oct. 29, 1982 at page 1, column 2) reported the isolation, synthesis, and biological activity of a group of related substances they have called growth hormone releasing factor (GRF). This factor has been sought after for decades by scientists but such search has been, until now, unrewarding due to the minute quantities in which such substance occurs naturally.

The successful isolation of GRF has been due in part to the discovery of the ectopic production of GRF in large amounts by pancreatic tumors, associated with acromeglay. Three forms of GRF derived from the pancreatic tumor have been observed. These forms consisting of three homologous peptides of 44, 40 and 37 amino acids in length are identical at the amino terminal and differ in the termination point of the carboxyl terminal. The 44 amino acid GRF is further distinguished in having an amide group at the carboxy terminus whereas the other two forms have a free carboxy group at that terminus.

The amidated form of GRF-44 is apparently the parent molecule and has been indicated to process the highest biological activity in vitro. However, all three peptides have been found to be virtually equally potent in vivo. It has further been shown that the removal of the amino terminal tryosine from GRF results in complete loss of bioactivity indicating that the active core of the molecule starts with the first amino terminal amino acid.

Growth in animals is believed to be regulated by a cascade of bio-regulatory molecules. Thus, the hypothalmus produces GRF which in turn acts upon the pituitary to cause release of growth hormone. The pituitary is maintained under negative feedback control by somatostatin and insulin growth factor (IGF). GRF has been found to be enormously active, exhibiting an $ED_{50}$ of approximately 50 fmole/ml or 75 pg/ml and has been found to release micrograms/ml levels of growth hormone in the blood. Thus, GRF can be utilized therapeutically in most of the areas now considered candidates for treatment by growth hormone. Examples of such therapeutic uses include the treatment of pituitary dwarfism, diabetes resulting from abnormalities in growth hormone production, enhancement of wound healing, treatment of burns and retardation on the aging process. Due to its favorable potency compared to growth hormone itself, GRF will have major advantages in the agricultural field as well. Agricultural uses would include, for example, stimulating development of fowl or animals raised for meat so as to allow either marketing at an earlier time or else allow the farmer to produce a larger animal per equal time on feed to present methodology. In addition, GRF would be useful in stimulation of milk production in dairy cows and increasing egg production in chickens.

While GRF in its various forms is of a molecular size which would allow for synthesis by either conventional solid phase or solution phase peptide synthetic methods, it is believed that for economic, large scale production of these therapeutically valuable substances the use of recombinant DNA technology is preferred.

There are examples already known in the art for producing recombinant mammalian peptides utilizing genes synthesized by chemical methods. Thus, for example, in Science 198, page 1956 (Dec. 9, 1977) there is reported the production of recombinant human somatostatin in E. coli utilizing a chemically synthesized gene. This gene was fused to the E. coli beta-galactosidase gene on the plasmid pBR 322. Transformation of E. coli with the chimeric plasmid DNA lead to the synthesis of a polypeptide including the sequence of amino acids corresponding to somatostatin. Biologically active somatostatin was specifically cleaved from the chimeric protein by treatment with cyanogen bromide. This procedure is described in greater detail in U.K. Patent Application No. 2,007,675A. More recently substantially larger synthetic genes have been synthesized and cloned such as, for example, the gene for human leukocyte interferon.

SUMMARY OF THE INVENTION

According to one aspect of the invention there is provided a method of preparing structural genes coding for the microbial expression of each of the known forms of GRF. Such method involves preparing a series of oligodeoxyribonucleotide fragments which are assembled by:

(a) preparing a first series of oligodeoxyribonucleotide fragments which, when joined in the proper sequence, yield a DNA coding strand for the amino acid sequence of the desired GRF form;

(b) preparing a second series of oligodeoxyribonucleotide fragments which, when joined in proper sequence, yield a DNA strand complementary to the coding strand;

(c) effecting hydrogen bonding between mutually complementary portions of the first and second series fragments to form a double-stranded structure; and (d) completing the respective strands by ligation.

The resulting gene codes for the expression of one of the desired GRF forms. In addition, according to a further aspect of the invention there is provided a double stranded polydeoxyribonucleotide having cohesive termini each comprising one strand of a double-strand restriction endonuclease recognition site and between the termini, a structural gene coding for the expression of a desired GRF form.

In a further aspect of the invention there is provided a recombinant microbial cloning vehicle comprising a first restriction endonuclease recognition site, a structural gene coding for the desired GRF form, and a second restriction endonuclease site. Such microbial cloning vehicle may then be used to transform a desired microbial host such as a yeast or bacterial host conventionally employed in recombinant technology to provide a microorganism which when fermented under proper conditions will provide expression of the desired GRF form in substantial quantities.

Finally, a further aspect of the invention involves the isolation and purification from the fermentation process of the desired GRF form so as to provide GRF essentially free of bacterial protein thus suitable for use as a therapeutic agent.

BRIEF DESCRIPTION OF THE DRAWINGS

The accompanying drawings illustrate aspects of the preferred embodiments of the invention, that is the procedure whereby expression of GRF by microorganism transformants containing recombinant plasmids can be achieved.

FIG. 2. A schematic structure of the gene sequence coding for the amino acid sequence of GRF-OH(44) is given. Also shown is the double-stranded gene with restriction endonuclease termini at either end for insertion into the expression vector.

FIG. 3. A schematic structure of a synthetic gene whose coding strand comprises codons for the amino acid sequence of GRF-44 is depicted. Additionally, restriction endonuclease recognition sites are shown. The GRF structural gene shown is flanked at both ends by appropriate $P_L$ linker sequences to allow ready insertion into the aforesaid cloning and expression vector. Note that while the peptide sequence of natural GRF(44) terminates in an amide group at the carboxy, the corresponding recombinant GRF terminates in a carboxy group and thus recombinant GRF(44) is hereafter designated GRF-OH(44).

FIG. 4. A series of 18 oligodeoxyribonucleotide fragments which are employed in the construction of the synthetic gene for GRF-OH(44) with $P_L$ linker termini are shown. The fragments which are associated with the prime nucleotide numbers represent the complementary gene strand.

FIG. 13. Sequences for substitution oligonucleotide fragments 14', 15' and 16' and a partial construction of a gene segment (ligation point indicated by arrow) containing these fragments, which unit can be ligated to gene segment 1-13 to form a structured gene for production of GRF-OH(37) is shown.

DETAILED DESCRIPTION

Preparation of Genes Coding for GRF

Figure 15:
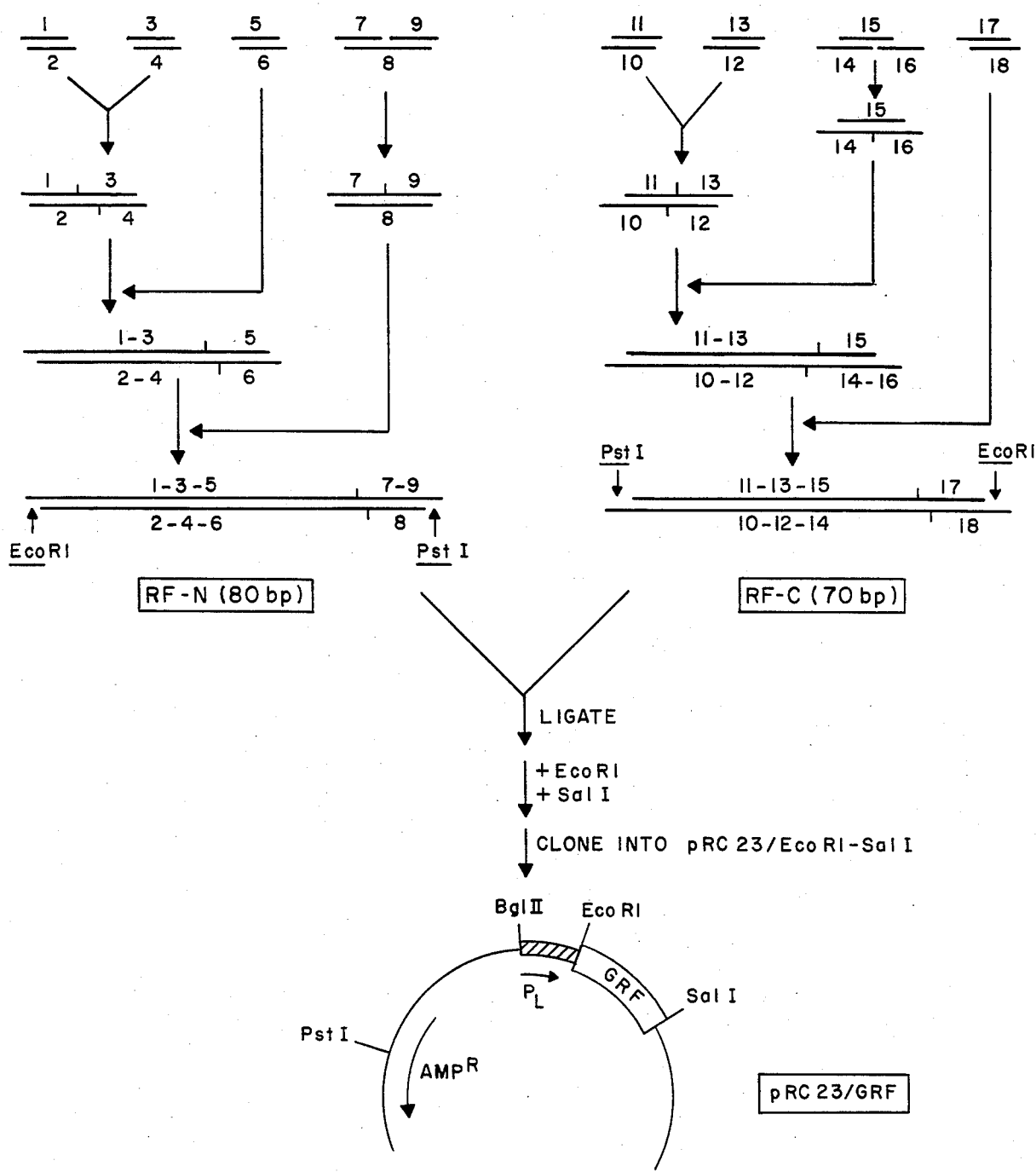
FIG. 15. A flow chart for the construction of a recombinant plasmid capable of expressing GRF-OH(44) using monomeric N and C fragments is shown.

DNA coding for any desired polypeptide form of GRF i.e. GRF-OH(44), GRF-OH(40) and GRF-OH(37) may be prepared by chosing codons according to the genetic code. For ease in preparation and purification, oligodeoxyribonucleotide fragments of, for example, from about 14 to about 20 nucleotides are prepared separately, and assembled to provide the desired sequences. Thus, one prepares a first and second series of oligodeoxyribonucleotide fragments of convenient size. The first series, when joined in proper sequence, yield a DNA coding strand for expression of GRF (see, e.g., FIG. 3, fragments 1, 3, 5, 7, 9, 11, 13, 15 and 17). The second series when likewise joined in proper sequence, yield a strand complementary to the coding strand (e.g., FIG. 3, fragments 2, 4, 6, 8, 10, 12, 14, 16 and 18). The fragments of the respective strands preferably overlap such that complementary promotes their self assembly through hydrogen bonding of the cohesive termini of fragment blocks. Following assembly, preferably in the two-step approach illustrated in FIGS. 5 and 6, for dimer N and C fragments or more preferably for monomer N and C fragments as seen in FIG. 15, the structural gene is completed by ligation in the conventional manner.

The degeneracy of the genetic code permits substantial freedom in the choice of codons for any given amino acid sequence. See for example, FIG. 2. For present purposes, however, codon choice was advantageously guided to provide a majority of the codons preferred in the expression of microbial genomes.

Thus the E. coli condon preferences were judiciously incorporated with codons for yeast expression so that the genes will be suitable for bacterial and yeast expression vectors. The gene sequence selected also provides convenient restriction sites which facilitate assembly of the gene and its subsequent analysis. The selected sequence for GRF was computer-scanned to ensure the absence of self-complementary and repeated sequences which might interfere with proper ligation of the oligonucleotides during assembly.

For expression in E. coli, the coding sequence for the GRF polypeptide is preceded by an ATG initiation codon and followed by a single TAA translational stop codon. EcoRI termini were placed at the beginning and at the end of the gene for convenient insertion into the expression vector(s). A Sal I site was also included following the coding sequence as an alternative site for insertion into the expression vector and to facilitate rapid Maxam-Gilbert sequencing of the gene once it is cloned.

Preparation of the Expression Vector

A plasmid, phage DNA or other DNA sequence which is able to replicate in the host cell and transform may be referred to herein as an expression vehicle, expression vector, or vector for the purposes of this invention. These vectors are characterized by one or a small number of endonuclease recognition or restriction sites at which DNA sequences may be cut in a determinable fashion without attendent loss of an essential biological function of the DNA, e.g., replication, production of coat proteins or loss of promoter or binding sites, and which contain a marker suitable for use in the identification of transformed cells, e.g., ampicillin resistance.

Preferred expression vectors used in the practice of the present invention further comprise hybrid ribosome binding sites. Ribosome binding sites (RBS) from which the hybrid RBS are derived, comprise RNA sequences encoded by the DNA. RBS's are necessary for the initiation of translation in a host cell. RBS's consist essentially of (1) an ATG translation initiation codon for the amino acid methionine (all known E. coli gene products begin with the amino acid methionine which may or may not be subsequently cleaved off); (2) A sequence of 3 to 9 bases which are complementary to bases at the 3' end of 16S ribosomal RNA known as Shine-Delgarno (SD) sequence Shine, J. and Delgarno, L. Nature 254, 34 (1975); and (3) a sequence of bases between the two known as linker region.

The expression vectors forming the preferred embodiment of this invention are derivatives of pBR 322 containing $P_L$ promoter isolated from bacteriophage lambda DNA and inserted between the $tet^R$ and the $amp^R$ genes. $P_L$ is a promoter of choice since it is a very strong promoter that can be efficiently and conveniently controlled by the lambda cI repressor. The gene encoding the repressor carries a mutation, CIts2 or cIts857, which renders the repressor temperature-sensitive. At 30° C. the repressor functions normally, and from about 37° C. to about 42° C. it is inactivated. Thus, the $P_L$ promoter is repressed (turned-off) at 30° C. and derepressed (turned-on) at 42° C. The ability to control the $P_L$ promoter allows one to grow the culture at about 30° C. to about 36° C. without expressing the gene product and an optimum time shift the temperature from about 37° C. to about 42° C. to produce the desired GRF product.

The preferred vector used in the present invention also contains an EcoRI restriction site distal (downstream in the 3' direction) the SD sequence, providing a means of constructing different hybrid RBS's. Once the hybrid RBS is constructed using the EcoRI site to join the SD sequence to the ATG coding sequence of the GRF coding gene, it can be further modified by restricting with EcoRl, filling-in the termini with Klenow Polymerase I and joining the two resulting ends by blunt-end ligation with $T_4$ DNA ligase.

It is also within the skill of the art to utilize other control elements to produce alternative expression vectors in conjunction with the novel structural genes for GRF provided by the present invention. Obviously some modification may be required in the termini provided to allow insertion of the gene into the requisite plasmids. Suitable systems for use in bacteria in the broadest aspects of this invention include the lac promoter-operator system, the arabinose operon (phi 80 dara) or the colicine El, galactose, alkaline phosphatase or tryptophan operons. Similarly the ADH system can be employed to provide expression in yeast.

The Microorganism

A large number of unicellular microorganisms are known in the art as being suitable for transformation. Particular microorganisms include bateria, fungi, and algae. Preferred organisms for transformation include bacteria such as strains of E. coli; Bacillaceae, such as Bacillus subtillis and the like. Yeasts form a further preferred group of microorganisms for transformation.

In a preferred embodiment of this invention, the micoorganism employed as the recipient in the transformation procedures in the microorganism E. coli K-12 strain 294 as described in British Patent Publication No. 2055382A. Strains of this microorganism has been deposited with the American Type Culture Collection, ATCC Accession Nos. 31446 and 31448 deposited Oct. 28, 1978. Other suitable, E. coli strains may also be employed, such as E. coli MA 210 or RR I.

The present invention is further illustrated by the following examples. In such examples procedures actually carried out are described in the past tense whereas the present tense is employed to describe prospective procedures.

Figure 1:
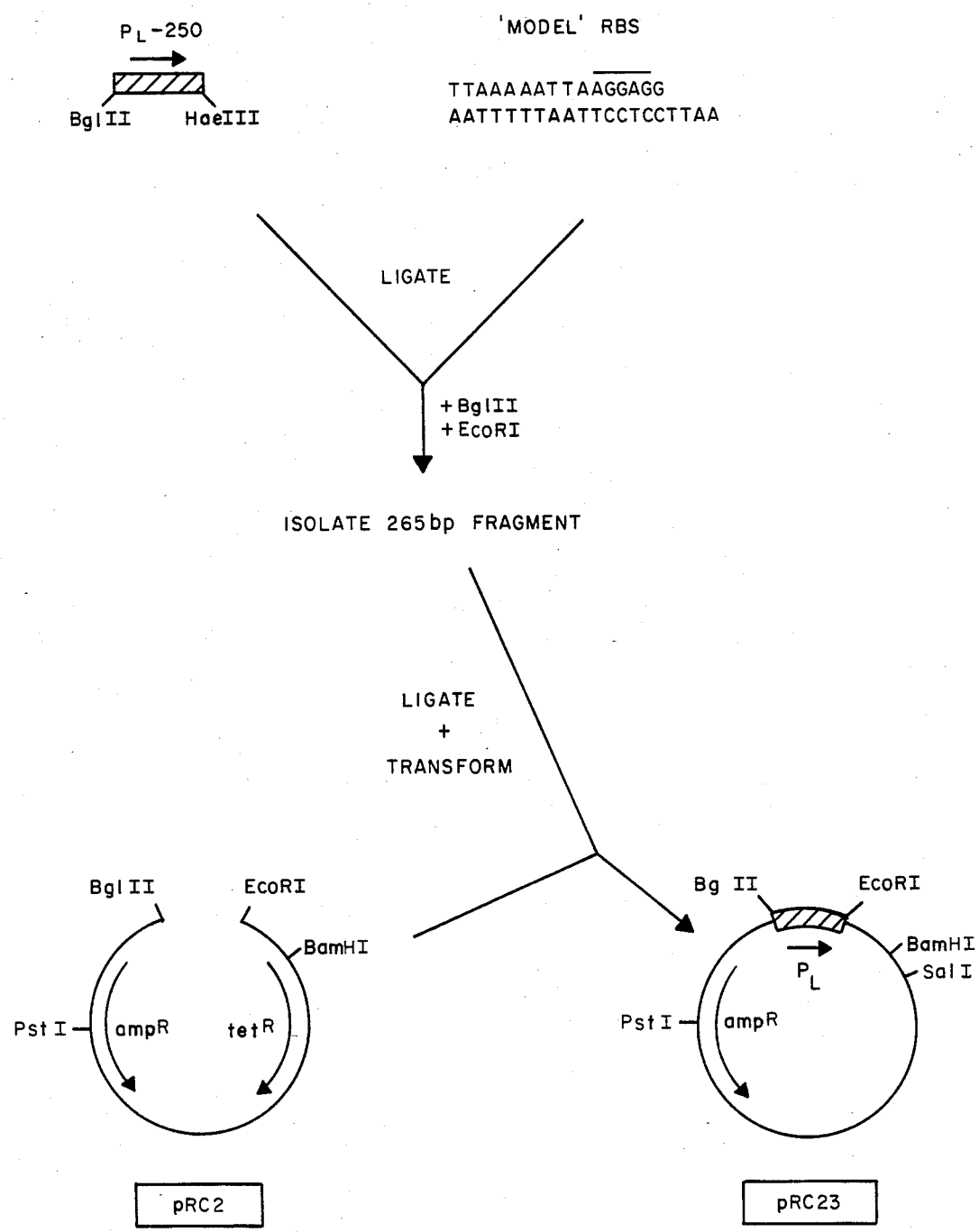
FIG. 1. A schematic outline of the process by which a preferred cloning and expression vector which promotes gene expression is derived from the bacteriophage lambda $P_L$ promoter is described. This vector identified as pRC23 is constructed by ligating synthetic oligonucleotides containing a "consensus" ribosome binding site (Scherer et al., *Nucleic Acids Research* 8, 3895 (1980)) to a 250 bp Bgl II-Hae III fragment containing the $P_L$ promoter and inserting the ligation product into the plasmid pRC2. Further details concerning the construction of the cloning and expression vector pRC 23 can be obtained by reference to U.S. patent application Ser. No. 397,388, filed July 12, 1982 entitled "Novel Vectors and Method for Controlling Interferon Expression", inventor Robert M. Crowl.

EXAMPLE 1 pRC23 was constructed by ligating synthetic oligonucleotides comprising a "consensus" RBS [Scherer, et al. Nucleic Acids Research, 8, 3895 (1980)] to a 250 bp Bgl II-Hae III fragment containing the lambda $P_L$ promoter, and inserting the ligation product into pRC2 as shown in FIG. 1. The details of this construction are described below.

In order to isolate the 250 (bp) base pair DNA fragment containing the lambda $P_L$ promoter, 1 μg of a 450 bp Bgl II-HPa I DNA fragment (from bp #35260 to 35710 of the November 1981 version of the lambda DNA sequence) was digested with Hae III and the products were isolated by preparative gel electrophoresis in 5% polyacrylamide. About 200 μg of the 250 bp Bgl II-Hae II fragment was ligated to 60 pmoles each of the synthetic oligonucleotides shown in FIG. 1 which comprise most of the "consensus" ribosome-binding site sequences generated by computer analysis as described in Scherer, et al. Nucleic Acids Research 8, 3895 (1980). The ligated molecules were digested with Bgl II and EcoRI (to eliminated oligomers) and purified by gel electrophoresis. The ligated products were then ligated into pRC2 which also had been digested with Bgl II and EcoRI. pRC2 is a derivative of pBR322 with a Bgl II site located adjacent to the EroRI site (see FIG. 1). Transformation of RR1 (pRK248cIts) was performed using standard methods and transformants were selected on media containing ampicillin (50 μg/ml) at 30° C. 50 transformants were obtained, DNA was isolated from 8 of those and analyzed by digesting with Hinc II. 6 of the 8 showed the expected restriction pattern and Maxam-Gilbert nucleotide sequence analysis of one of these confirmed the expected construction (designated pRC23).

EXAMPLE 2

Standard Method for Preparation of 3'-O-succinylnucleosides

The 5'-O-dimethoxytrityl and N-protected deoxynucleoside (2.5 mmole) is dissolved in dry pyridine (5 ml) and (0.3 g) N,N-dimethylaminopyridine. Succinic anhydride (2.0 mmole, 0.2 g) is added and the solution stirred at room temperature for 24 hr. After the reaction is completed, solvent is evaporated under vacuum and the dry gum is coevaporated with toluene (10 ml each time) twice. The residue is dissolved in methylene chloride (30 ml) and the solution extracted with citric acid (ice cold). The organic phase is washed twice with water (15 ml each) and then dried over anhydrous sodium sulfate. In order to avoid any detritylation of the product, about 0.3 ml of pyridine is added to the methylene chloride solution. The methylene chloride solution is concentrated to about 10 ml and the succinylated nuceloside is isolated by precipitation into hexane:ether (1:1, v/v; 250 ml). The precipitate is collected by filtration and dried in vacuo.

EXAMPLE 3

Figure 8:
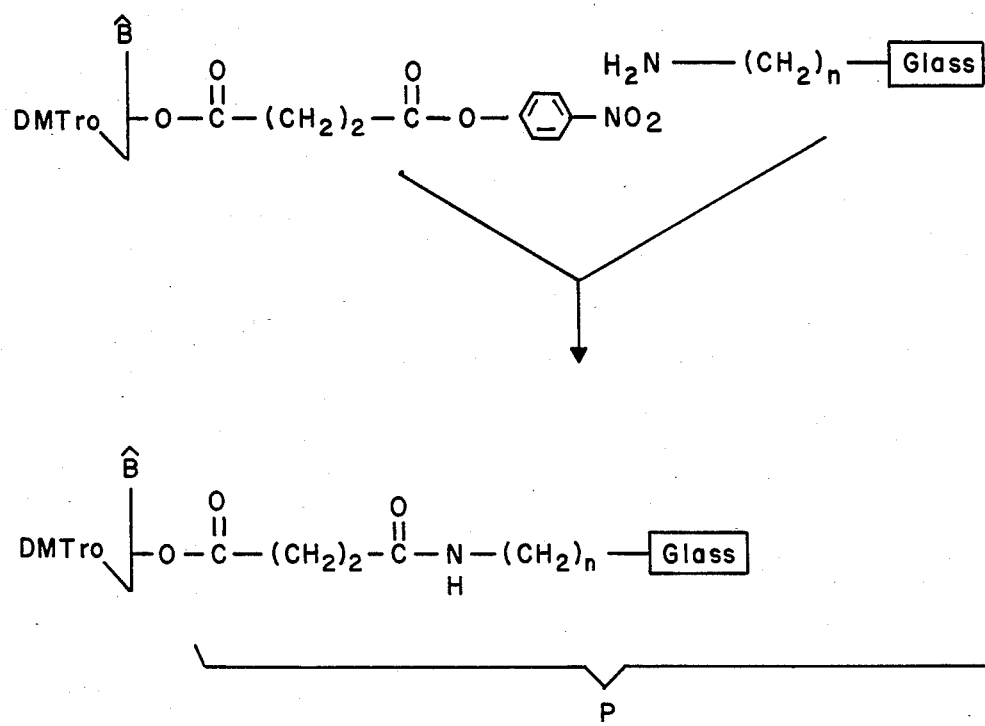
FIG. 8. A schematic outline of the loading of the glass support procedure utilized in the solid support phosphite methodology employed in the synthesis of oligonucleotides 1, 4, 5, 9, 11, 15 and 20 is described. The procedure is adapted from Matteucci and Caruthers, J. Am. Chem. Soc. 103, 3185 (1981).

Standard Method for Preparation of p-nitrophenyl esters of succinylated nucleosides As seen in FIG. 8 succinylated nucleoside (1 mmole) is dissolved in dry dioxane (3 ml) containing pyridine (0.3 ml). To the above solution is added dicyclohexylcarbodiimide (DCC) (~5 mmole, 900 mg) and p-nitrophenol (0.22 g, 1 mmole). The solution is stirred for 2 hr. The precipitate of dicyclohexylurea is removed by centrifugation. The supernatant is directly used for coupling to the resin as described in the next Example.

EXAMPLE 4

Condensation of Succinylated Nucleosides to the Resin for Solid Support Phosphite Methodology A 25 ml (~10 g) sample of Pierce CPG/Long Chain alkylamine controlled pore glass support (Pore diameter 500 Å, particle size 125–177μ) is suspened in 25 ml dry dimethylformamide (DMF). The solution containing the p-nitrophenyl ester of the succinylated nucleoside is added to the above suspension. The contents are shaken for 24 hr. The derivatized resin is isolated, washed with dry DMF (3 times, 30 ml each), dioxane (5 times, 30 ml each), methanol (5 times, 30 ml each) and finally with anhydrous ether (3 times, 30 ml each). Any unreacted amino functions are blocked by reacting the support with a solution of dry pyridine (25 ml), N,N-dimethylamino pyridine (250 mg) and acetic anhydride (5 ml) for 2 hr. at room temperature. The solid support is filtered and washed successively with methanol (5 times, 30 ml) and anhydroxy ether (2 times, 30 ml).

Determination of Nucleoside Loading on the Support

Approximately 1 mg quantity of the nucleoside-loaded resin is treated with 0.1M toluenesulfonic acid in acetonitrile (1 ml). The trityl carbonium ion released from the resin as a red-orange color is collected and diluted appropriately with acetonitrile to measure optical density at 498/μm. An average of 4 such measurements provided the extent of loading on the support. The range of loading obtained from several different resin loading experiments was 22–25 μmole of nucleoside/g of the solid support.

EXAMPLE 5

Figure 9:
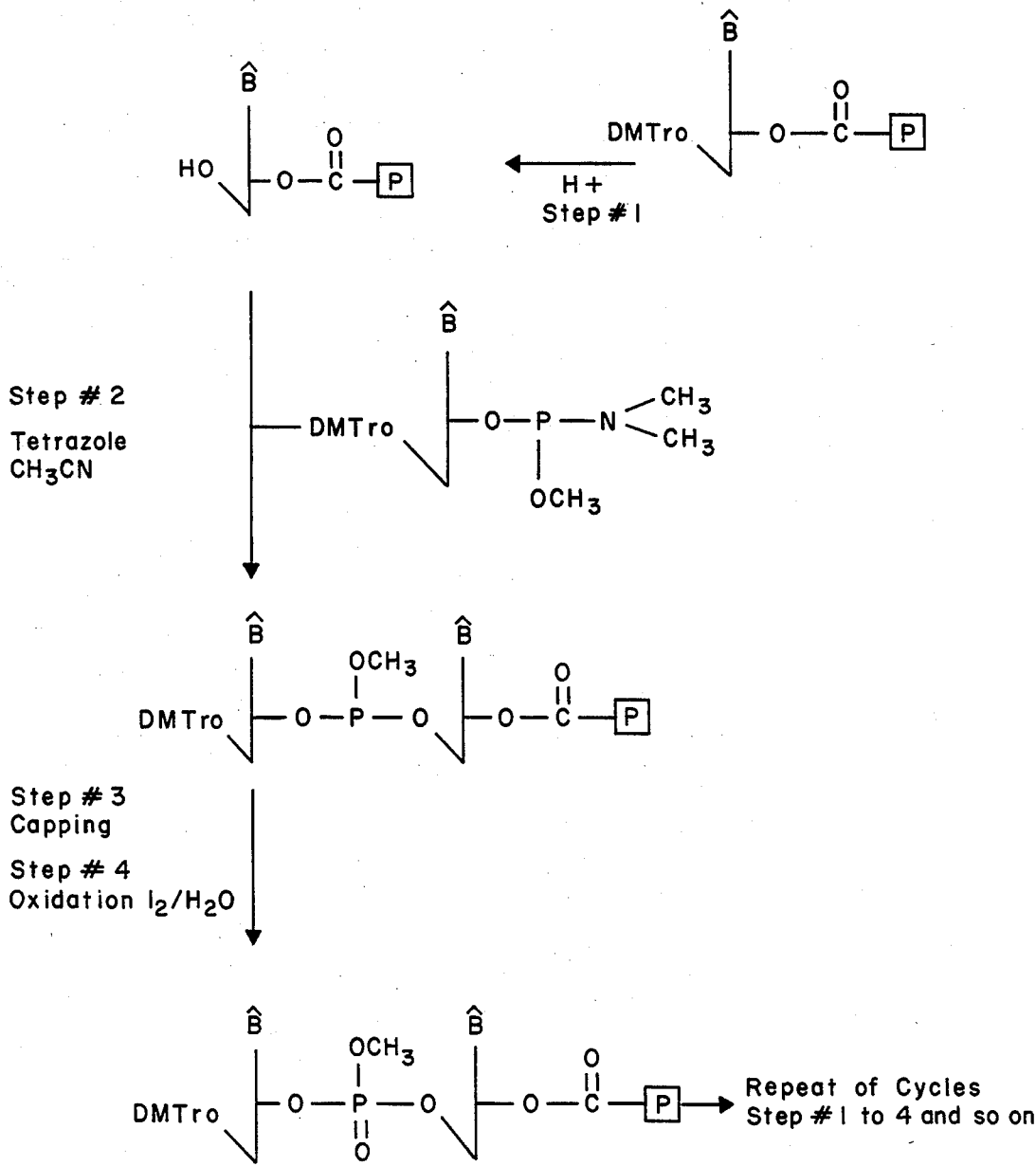
FIG. 9. A schematic outline of the oligonucleotide synthesis scheme using solid support phosphite method is shown.
Figure 10:
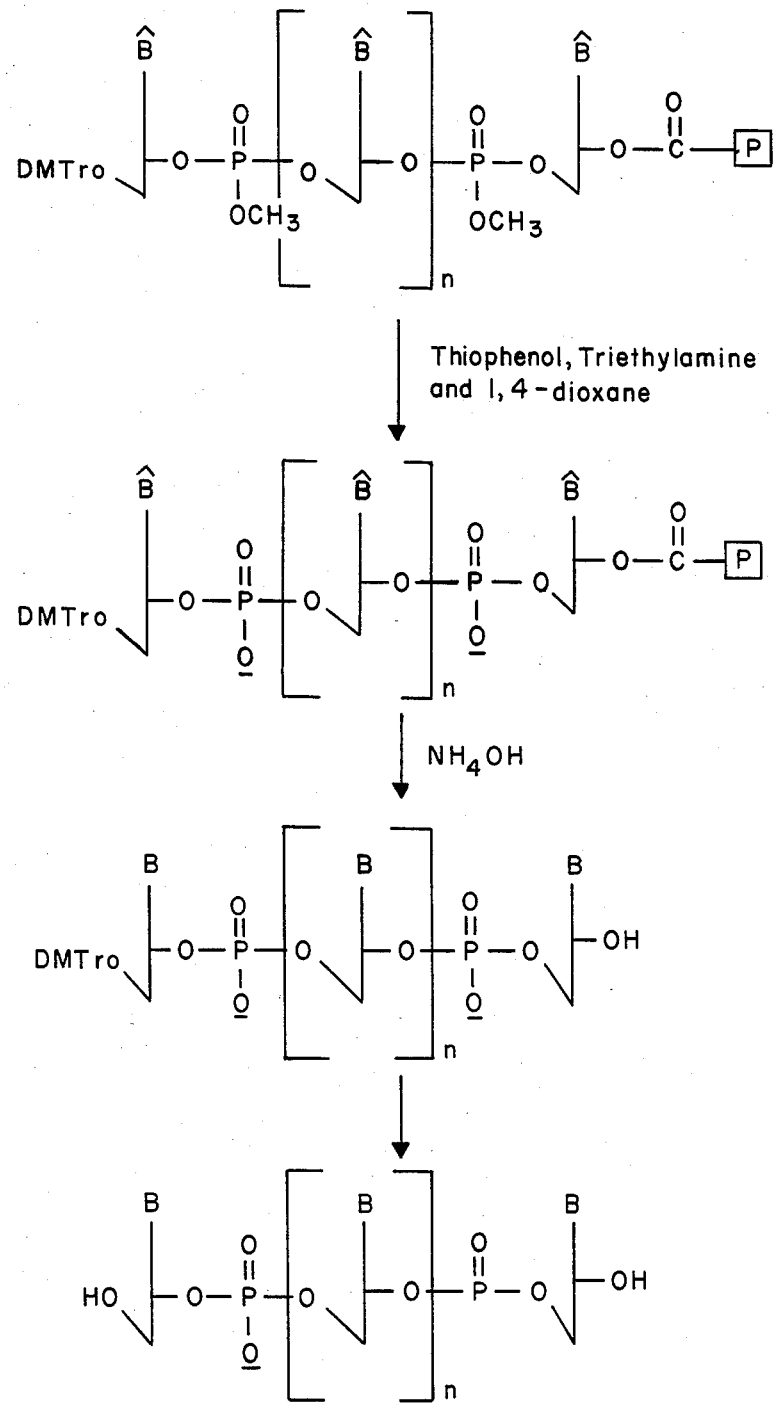
FIG. 10. A schematic outline of the deprotection and release of oligonucleotides from the solid support carried out in the solid support phosphite method is depicted.

Standard Preparation of 5'-O-dimethoxylnityl-3'-O-Phosphoroamidite Derivatives of Nucleosides As seen in FIG. 9 and following the procedure of Beaucage and Caruthers, Tetrahedron Letters 22, 1859 (1981), a sample of 5'-O-dimethoxytrityl nucleoside (5 mmole) is dissolved in dry and acid-free chloroform. To the solution is added diisopropylethyl-amine (2.74 ml, 15.74 mmole) followed by a gradual addition of dimethylamino-methyl phosphonomonochloridite $(CH_3OP(Cl)N(CH_3)_2)$ over 1–2 minutes. The reaction mixture is transferred to a separatory funnel with 175 ml of ethyl acetate. The organic mixture is extracted with saturated brine (4 times, 75 ml). The ethyl acetate phase is dried over anhydrous sodium sulfate. The solution is concentrated in an oil and then redissolved in dry ethyl acetate to obtain 50 ml of the solution. This solution is dropwise added to precooled (ice-acetone temperature) n-hexane (250 ml) for precipitation of the product which is then filtered and dried under high vacuum for 17 hr. at room temperature. For all four nucleoside derivatives yields of ~80% have been achieved. The samples of the dimethylamino phosphoroamidites were stored under argon at −14° C.

EXAMPLE 6

Solid Support Synthesis of Fragment No. 1

5'-AATTCTATGTATGCTGA-3' by Phosphite Methodology

Step 1: A sample of 5'-O-dimethoxytrityldeoxyadenosine-loaded glass support (435 mg, 10 μmole of dimethoxytrityl deoxyadenosine/g of support) was detritylated with 0.2M dichloroacetic acid in dichloromethane (2 ml) by shaking the suspension for 1.5 min. The support was washed with dichloromethane (2 times, 5 ml). A repeat of dichloroacetic acid treatment for a few seconds was given to insure completion of detritylation.

The support was washed successively as follows:
(a) with 1% triethylamine in dichloromethane (2 times, 5 ml)
(b) with anhydrous acetonitrile (9 times, 3 ml).

Step 2: A solution of dimethylaminophosphoramidite derivative of dimethoxytrityl deoxyguanosine (100 umole in 2 ml anhydrous acetonitrile) was added to the support followed by the addition of tetrazole solution (250 μmole in 2 ml of acetontrile). The suspension was shaken for 5 minutes, vacuum filtered and washed with anhydrous acetonitrile (4×5 ml).

Step 3: A 2 ml solution of acetic anhydride (0.4 ml) in pyridine containing ~10 mg of N,N-dimethylaminopyridine was shaken with the support for 2 minutes to block any unreacted hydroxyl functions and then the blocked support was washed with acetonitrile (4 times, 5 ml).

Step 4: A solution of iodine (0.2M) in tetrahydrofuran:water:2,6-lutidine (v/v 2:1:1) was shaken with the blocked support for 0.5 minute washed with dry acetonitrile (6 times, 5 ml) and washed with dichloromethane (2 times, 5 ml).

Step 1 is then repeated with the product of Step 4. Step 2 is then repeated with the phosphoroamidite derivative of 5'-O-dimethoxytrityl thymidine. Steps 3 and 4 are tthen repeated.

These cycles of Steps 1 through 4 are then repeated over and over with the addition of each successive nucleoside derivative, thus extending the chain in the 5'-direction by adding corresponding phosphoramide derivatives of deoxycytidine (dC), deoxyguanosine (dG), thymidine (T), deoxyadenosine (dA), T, dG, T, dA, T, dC, T, T, dA and dA respectively to yield the desired fragment.

EXAMPLE 7

Deprotection and Release of the Oligonucleotides from the Support

A sample of the oligonucleotide-bound support obtained in Example 6 (150 mg) was treated with a mixture of 1,4-dioxane (0.25 ml), 0.25 ml anhydrous triethylamine and 0.125 ml thiophenol for 30 minutes at room temperature. The resin was filtered, washed with methanol (4×2 ml) and hydrolyzed with concentrated ammonium hydroxide for 17 hours at 50° C. The resin was pelleted and the supernatant concentrated under vacuum and redissolved in water (1 ml). The solution of the oligonucleotides was passed through a 0.45 micron filter to remove very fine suspension and then fractionated on a high performance liquid chromatographic (HPLC) system using a C 18 reverse phase Microbondapak (Waters Assoc.). Column under a gradient of acetonitrile 10-30% in 0.05M triethylammonium acetate, pH 7.0, at 50° C. The well separated dimethoxytrityl containing product was collected, concentrated and treated with 80% aqueous acetic acid for 0.5 hr at room temperature. After evaporation of acetic acid, the sample was dissolved in water and extracted with ether to remove trityl alcohol. The aqueous layer containing the desired oligonucleotide was separated and examined for its purity on HPLC. In several cases a second purification at this stage was found necessary to obtain homogeneous product. Final criterion of purity was analysis of the 5'-$^{32}$P-labeled oligonucleotide on acrylamide gel electrophoresis under denaturing conditions. The nucleotide sequence of the fragments was ascertained by the Maxam-Gilbert method, Proc. Nat. Acad. Sciences (USA) 74, 560 (1977).

Following the same approach as described above, synthesis of the fragments 4, 5, 9, 11, 15 and 18 is accomplished.

EXAMPLE 8

Figure 11:
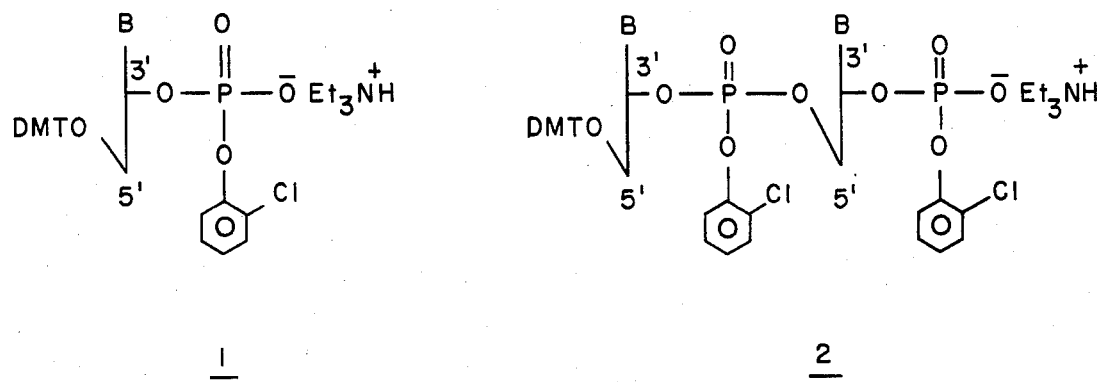
FIG. 11. A generic representation of the functional intermediates used in the solid support triester methodology employed for the preparation of fragments 2, 3, 6, 7, 8, 10, 12, 13, 14, 16 and 17 is shown. The procedure is adapted from Dembek et al. J. Am. Chem. Soc. 103, 706 (1981).
Figure 12:
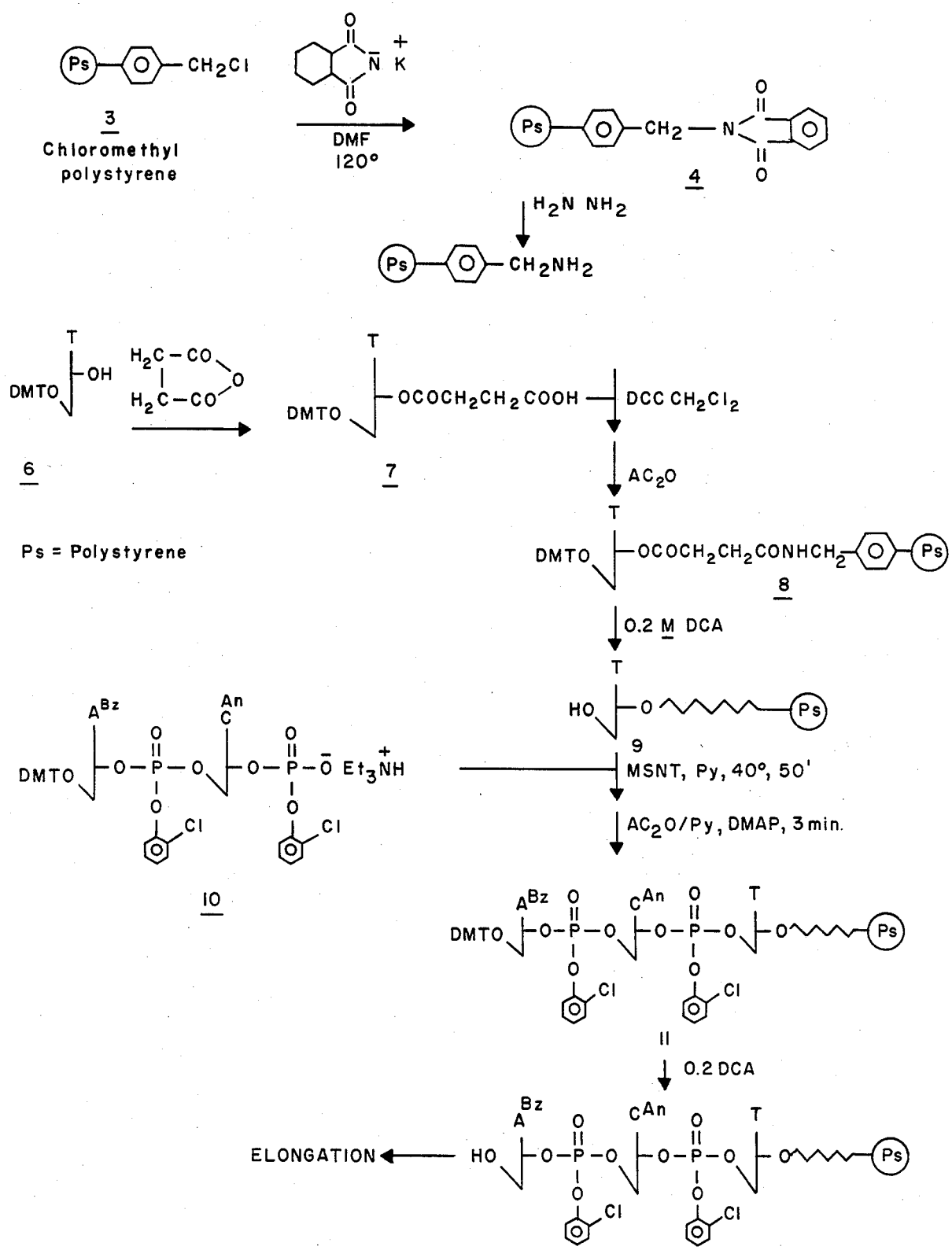
FIG. 12. A schematic outline of the reaction scheme employed in the construction of oligonucleotide fragments by the solid support triester method is shown.

Standard Method For Phosphotriester Solid-Phase Synthesis of Heptadecanucleotide d(CGCGATCTTCACTAACT), Fragment 3 GRF Gene Scheme 1 set forth in FIG. 12 outlines the essential steps involved in the solid-phase synthesis of fragment 3 of the GRF gene by the phosphotriester method. All numbers of compounds referred to in this Example relate to FIG. 11 or 12. These steps are:

a: Synthesis of suitably blocked mono- and dinucleotides of the general structure 1 and 2 respectively. (see FIG. 11)

b: Preparation of aminomethyl polystyrene resin 5 c: Loading of succinate 7 on to the aminomethyl polystyrene 5 and masking of any unreacted amino group with acetic anhydride-pyridine d: Removal of 5'-dimethoxytrityl group of polymer supported nucleoside 8 with 0.2M dichloroacetic acid (DCA) in $CH_2Cl_2$ to afford a 5'-hyroxy function (resin 9) for the coupling reaction e: Condensation of the triethylammonium salt of the dimer, AC 10 with 9 to provide polymer supported trinucleotide 11. Any unreacted 5'-OH group from 9 is masked with 10% acetic anhydride in pyridine f: detrylation of 11 with 0.2M DCA to generate a new 5'-OH group for the next coupling.

The aforesaid suitably protected mono-dinucleotides were synthesized according to procedures known in the art with slight modifications. 3'-succinate 7 of 5'-dimethoxytrityl-thymidine 6 was prepared according to the method published by Miyoshi et al., Nucleic Acids Research, 8, 5491 (1980).

Aminomethyl Polystyrene Resin 5

A slurry of commercially available chloromethyl polystyrene (1% cross linked, 0.32 mmol/g Cl$^-$) (30 g, 9 mmol) and potassium phthalimide (2.77 g, 15 mmol) in DMF 250 ml) was heated at 120° for 20 hours. The resin was then filtered while hot and washed consecutively with hot DMF (200 ml), water (4×50 ml), dioxane (3×80 ml), ethanol (3×80 ml) and ether (3×50 ml) to give the phthalimide derivative 4 which was suspended in ethanol (350 ml) and refluxed with hydrazine (5 ml) for 5 hrs. The reaction mixture was filtered and washed with hot ethanol (4×70 ml), hot DMF (2×70 ml), water (3×70 ml), ethanol (3×70 ml) and ether 3×80 ml). The resin was then dried (28 g) to give aminomethyl polystyrene 5. Picric acid titration showed amino group concentration of 0.21 mmol/g.

Loading of 5'-Dimethoxy-3'-0-succinyl-thymidine 7 on to the Aminomethyl Resin 5

To a slurry of aminomethyl resin 5 (5 g) in dry $CH_2Cl_2$ (30 ml) was added monosuccinate 7 (0.97 g, 1.5 mmol), DCC (0.927 g) and dimethylaminopyridine (DMAP) (50 mg) and the reaction mixture was allowed to stir at room temperature for 4 hrs. After filtering, the resin 8 was washed with $CH_2Cl_2$ (4×15ml), MeOH (4×15 ml), $CH_2Cl_2$ (4×15 ml) and ether (3×10 ml). After drying the resin 8 under vacuum (0.1 mm Hg), the concentration of the loaded nucleoside was determined by measuring the absorption spectrum of the liberated tritanol from the support in a 1% BSA solution in $CHCl_3$ [λ max 498, ε 92100] and was found to be 0.185 mmol/g.

Masking of the unreacted amino group from the resin 5, present along with resin 8, was achieved by reacting the entire mixture of the resins with 10% acetic anhydride-pyridine mixture (30 ml) containing dimethylaminopyridine (DMAP) (30 mg) for 30 minutes at room temperature. The resin was then washed with $CH_2Cl_2$, MOH, $CH_2Cl_2$ and ether. The concentration of the loaded nucleoside was again determined as described before and was found to be 0.178 mmol/g.

Detritylation of the Resin 8 with 0.2M Dichloroacetic acid in $CH_2Cl_2$

Table 1 below shows the conditions used for detrilation of each of the dimethoxytrityl group of each of the four nucleosides. A typical experiment is as follows: the resin was first swollen in dry $CH_2Cl_2$ (2 ml) for about 30 seconds in a small column (1.3×10 cm) and then shaken with 10 ml of 0.2M DCA for 30–40 seconds followed by a very quick filteration and very quick wash with $CH_2Cl_2$ (3–4 ml). This process was repeated (see table 1) until the washings did not show any color due to tritanol. The washings were collected and the absorption spectrum measured to determine the concentration of the tritanol evolved which, in turn, reflects the concentration of the loaded mono- or dinucleotide.

After complete detritylation had been achieved, the resin 9 was washed with 0.5M $Et_3N$ solution in $CH_2Cl_2$ and then with $CH_2Cl_2$ (3×10 ml) and pyridine (3×5 ml).

TABLE 1

| (DMT)N | Number of Operation with 0.2 M DCA | Time for each operation | Washings with $CH_2Cl_2$ |
|---|---|---|---|
| T | 5 × 10 ml | 40 sec. | 1 × 3 ml |
| C | 5 × 10 ml | 30 sec. | 1 × 3 ml |
| G | 3 × 10 ml | 30 sec. | 1 × 3 ml |
| A | 4 × 10 ml | 20 sec. | 1 × 3 ml |

Coupling of AC dimer 10 with 5′-hydroxy-polystyrene support 9 to give the polymer-supported ACT trimer 11

The 5′-hydroxy resin 9 (57 mg, 0.01 mmol) which had been washed with pyridine (see above) was dried under high vacuum (0.05 mm Hg) and by blowing hot air on the column from a heat gun for 2 minutes. The vacuum was carefully released by letting in dry air or argon. To the resin was then added a pyridine (0.7 ml) solution of the triethylammonium salt 10 (0.06 mmol) of the AC dimer followed by the addition of mesitylenesulfonyl-3-nitro-triazole (MSNT) (0.18 mmol). The column was properly stoppered and heated at 40° for 50 min. The reaction mixture was filtered and washed thrice with pyridine (3 ml each time). Any unreacted 5′-OH group was masked by reacting the resin with 10% $AC_2O$/Py containing DMAP (10 mg) for 3 minutes at RT. The resin was filtered and successively washed with pyridine (2×2 ml), $CH_2Cl_2$ (2×5 ml), MeOH (2×5 ml) and again with $CH_2Cl_2$ (2×5 ml) to afford the ACT trimer 11 supported by polystyrene polymer.

The 5′-dimethoxytrityl group of the resin 11 was removed with 0.2M DCA as described above (Table 1) and 5′-hydroxy resin 12 resulting therefrom was extended to the desired heptadecanucleotide by repeating each cycle with a dimer or a monomer of choice. The average coupling yield estimated by the absorption spectrum of the tritanol liberated from the support was 94%.

Deblocking and Purification

After the last coupling reaction, the resin (50 mg) was treated with 0.5 molar solution of $N^1$, $N^1$, $N^3$, $N^3$-tetramethylguanidinium pyridine-2-carboxaldoximate (1 ml) in 80% dioxane-$H_2O$ for 15 hours at room temperature according to the procedure of Reese et al., Tet. Letters, 19 2727 (1978). The solvent was then evaporated off, the residue left was treated with concentrated ammonia (28%) (4 ml) at 60° for 8 hrs. After centrifugation, the supernatant was concentrated to a volume of ca 0.5 ml which was dissolved in 0.05M TEAB (1.5 ml) and passed through a Sephadex G-50 column using 0.05M TEAB as a mobile phase. The excluded fractions (6 ml each) were collected and the absorption measured on a Beckman UV spectrophotometer Model 34. The fractions 30–33 containing the product were collected to give 100.8 ODs. 50 ODs out of this product were purified by high-performance liquid chromatography (HPLC) on a microbondapak $C_{18}$ column (waters) using a linear gradient of 7.5 to 37.5% acetonitrile (pH 7.8) over a period of 12 minutes. Peak 2 eluting with 31% $CH_3CN$, contained the dimethoxytrityl product and was collected to give 30.2 ODs. The solvent was evaporated off, the residue left was detritylated with 80% acetic acid (20 minutes at room temperature). Acetic acid was evaporated off and the residue left was co-evaporated with toluene (3×1 ml) to remove residual acetic acid. The resulting residue was dissolved in water (2 ml), and extracted with ether (3×3 ml) to remove any organic impurities. The aqueous solution was carefully concentrated to a volume of 400 μl, filtered and purified on a microbondapak $C_{18}$ HPLC column using a linear gradient of 7.5–37.5% acetonitrile. The peak eluting with 20.6% acetonitrile was collected and further purified by electrophoresis on an acrylamide gel in the presence of 7M urea. The slowest moving band was isolated by buffer elution and after labelling the 5′-hydroxyl group with $\gamma[^{32}P]$-ATP, the sequence of the heptadecanucleotide fragment 3, was confirmed by Maxam-Gilbert sequence analysis.

Following the same approach as described above, synthesis of the fragments 2, 6, 7, 8, 10, 12, 13, 14, 16 and 17 is accomplished.

EXAMPLE 9

Dimer Construction·

Figure 5:
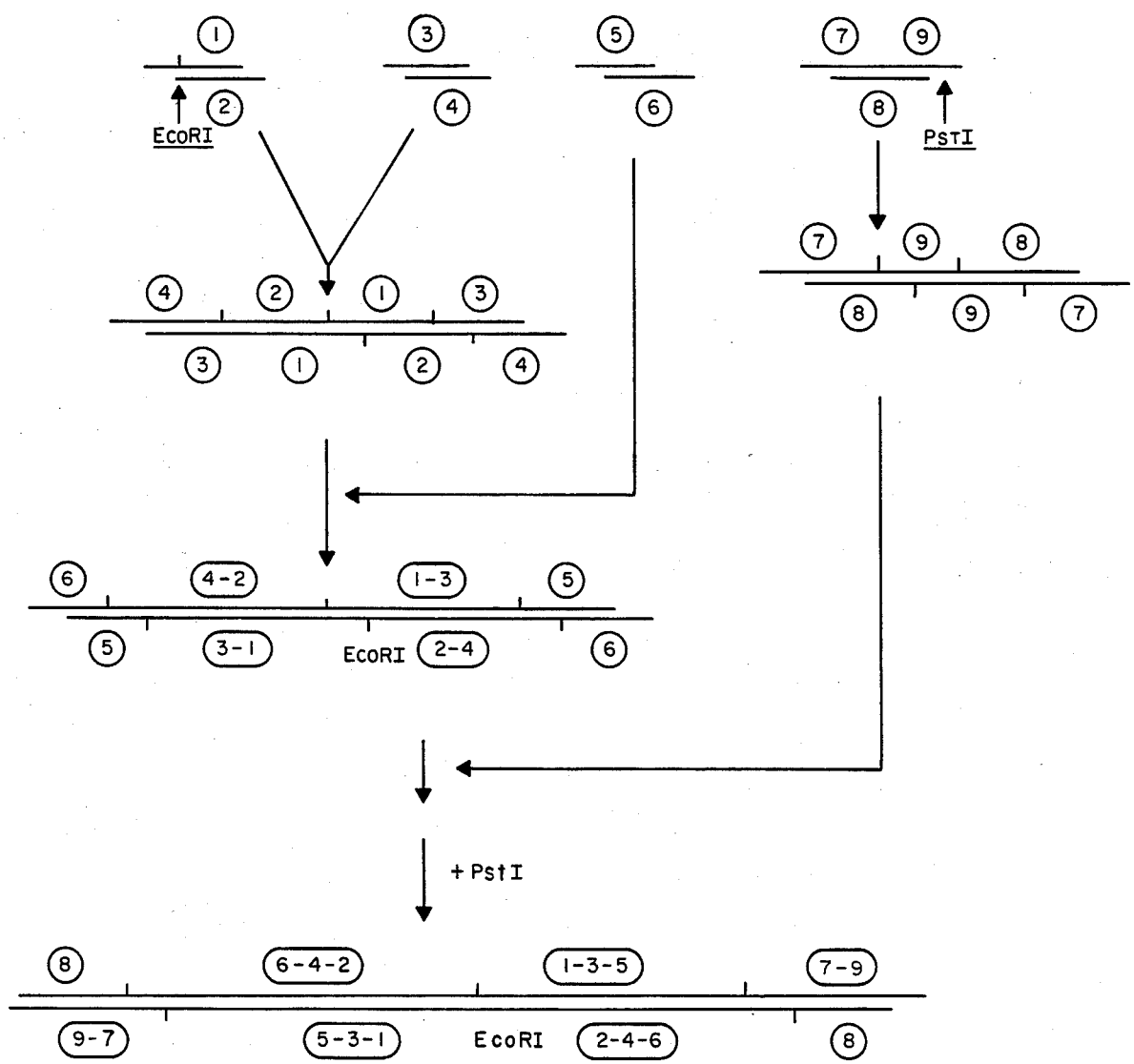
FIG. 5. A flow chart for the construction of a 160 bp segment of the synthetic gene for GRF-OH(44) containing the amino terminal section. The appropriate number fragments in FIG. 4 are utilized.
Figure 6:
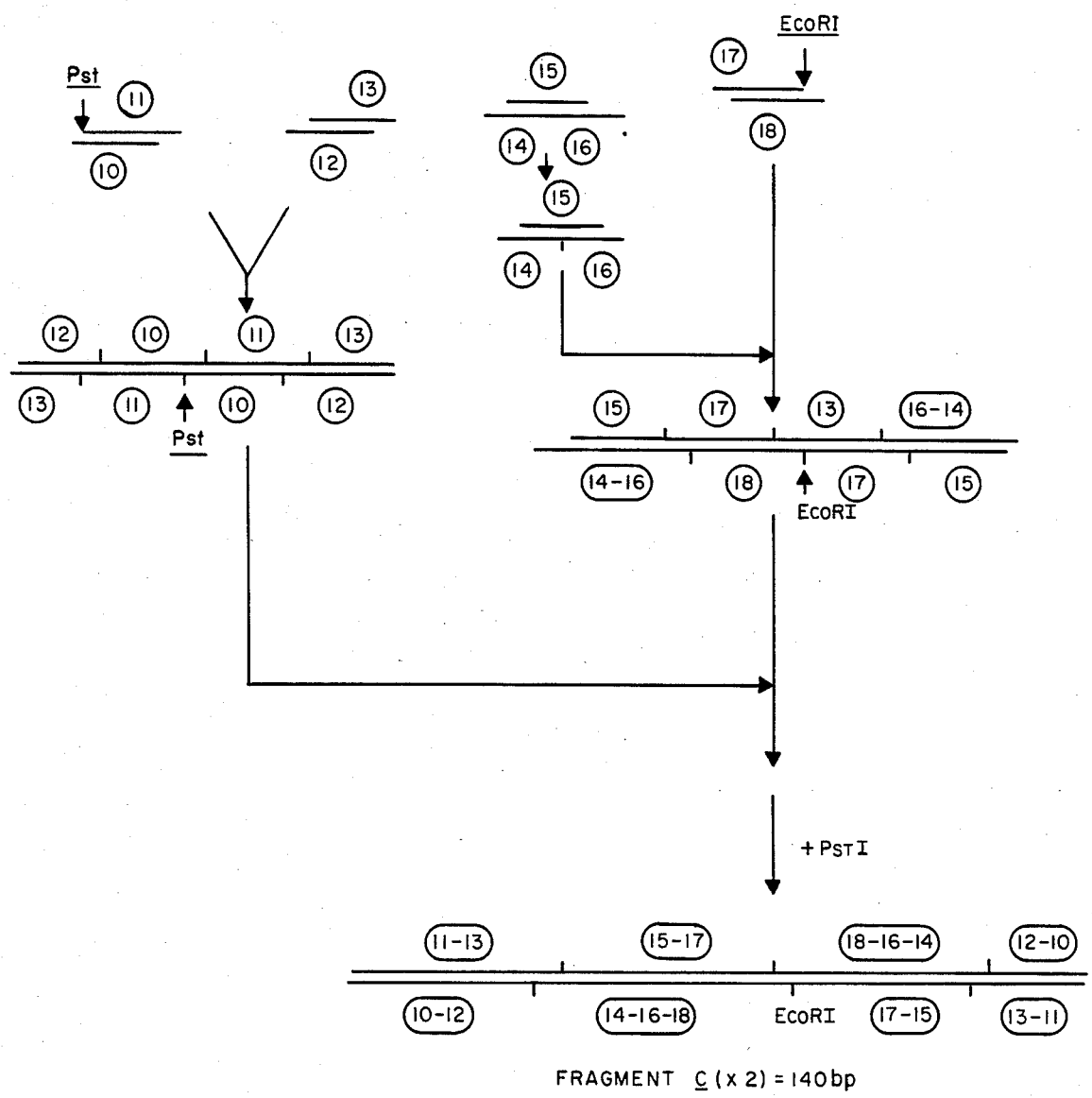
FIG. 6. A flow chart for the construction of a 140 bp fragment of the synthetic gene containing the carboxy terminus of GRF-OH(44) is depicted.
Figure 7:
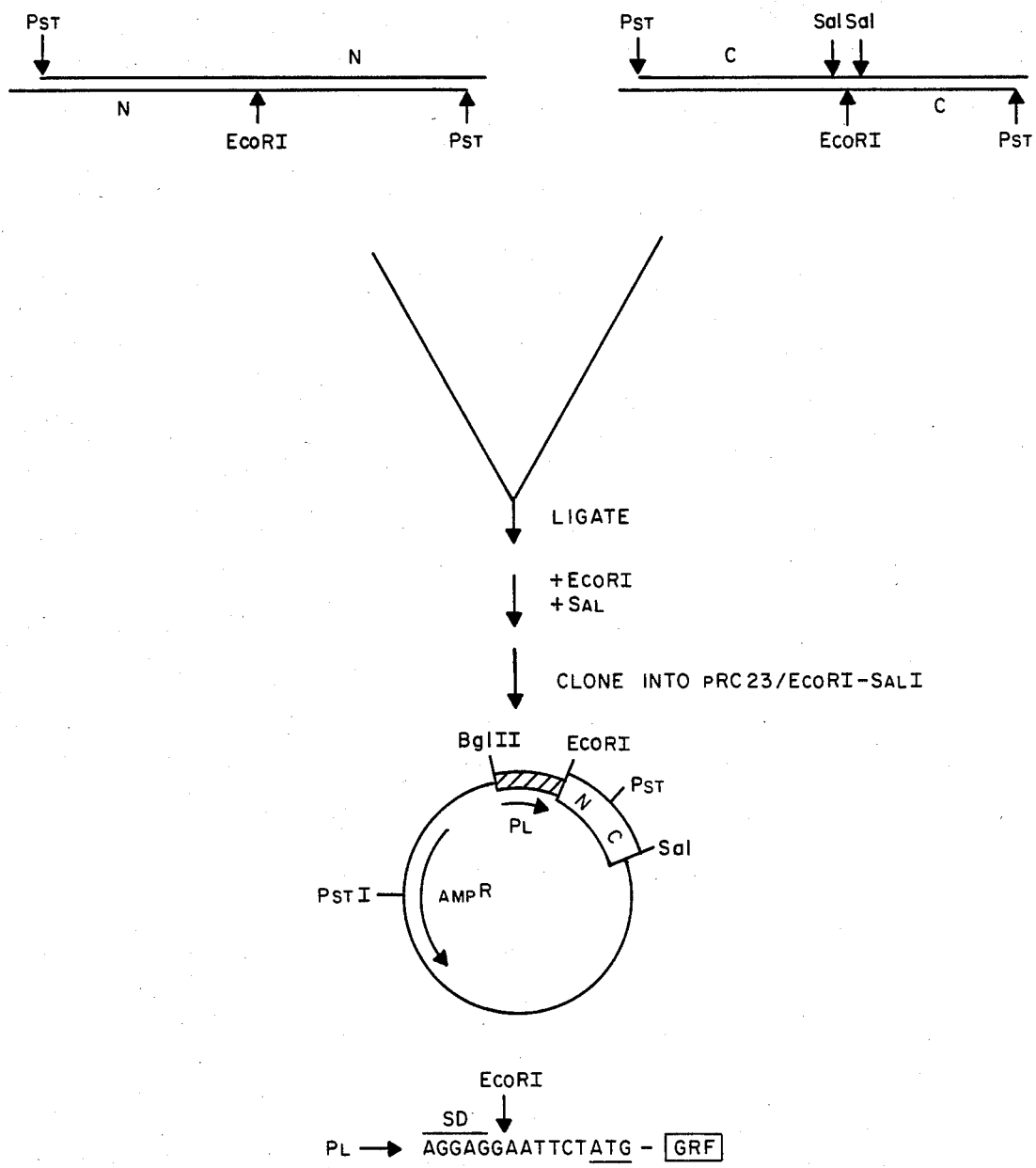
FIG. 7. A flow chart for the construction of a recombinant plasmid capable of expressing GRF-OH(44) beginning with the parental plasmid pRC 23 is shown. As seen in this Figure the N and C fragments of the GRF snythetic gene are first ligated and then inserted into the indicated plasmid. Amp$^r$ denotes the gene for ampicillin resistance. The relative positions of various restriction endonuclease specific cleavage sites on the plasmid is depicted (e.g. Pst I, Bgl II, EcoRI, Sal, etc.). Note that the gene for tetracycline resistance (Tet$^r$) normally found in pRC 23 is eliminated when the restriction cut at the Sal site is made. Thus the recombinant plasmid exhibits only ampicillin resistance for screening.

As outlined in FIGS. 5 and 6, the oligonucleotides are assembled in two stages. Oligonucleotides #1–9 are ligated following the scheme in FIG. 5 to generate fragment N, the amino-terminal half of the GRF gene. Likewise, oligonucleotides #10–18 are ligated to generate fragment C, the carboxy-terminal half of the gene as seen in FIG. 6. Dimers of N and C are cloned individually into the Pst I site of pBR322 (322 (see Bolivar et al, Gene 2, 95 (1977) to take advantage of insectional inactivation of the beta-lactamase gene as an initial screen of the transformants. Plasmid DNA from transformants showing a $tet^R$ $amp^S$ phenotype are further analyzed to confirm that the correct fragments are cloned. After amplification of the plasmid DNA carrying N and C, the fragments are excised by digesting with Pst I and purified by preparative gel electrophoresis. The dimers of N and C are then ligated together and digested with EcoRI and Sal I to generate the monomeric form of the completely assembled GRF gene (see FIG. 7).

Specific procedures for the aforesaid ligations are set forth below:

300 pmoles of each of the oligonucleotides (#1–18) are phosphorylated with T4 polynucleotide kinase in 20 μl reaction mixtures containing 50 mM Tris-HCl (pH 7.4), 10 mM MgCl$_2$, 0.1 mM Na$_3$EDTA, 5 mM DTT, 0.1 mM Spermidine-HCl, and a 5-fold molar excess of ATP ($\gamma$-$^{32}$P-ATP) at 37° for 30 minutes.

Equimolar amounts of each oligonucleotide are ligated under standard conditions (50 mM Tris, pH 7.4, 10 mM MgCl$_2$, 10 mM DTT, 0.3 mM ATP) with 4 units of T4 DNA ligase at 15° for 3–12 hours. Ligation reactions are monitored by gel electrophoresis in 20% polyacrylamide, and where necessary, the ligation products are purified by preparative gel electrophoresis.

Monomer Construction

As outlined in FIG. 15, the oligonucleotides were assembled in two stages. Oligonucleotides #1–9 were ligated following the scheme in FIG. 15 to generate fragment RF-N, the amino-terminal half of the GRF gene. Likewise, oligonucleotides #10–18 were ligated to generate fragment RF-C, the carboxy-terminal half of the gene as seen in FIG. 15.

Specific procedures for the aforesaid ligations are set forth below:

20 p moles each of the synthetic fragments #1–18 were phosphorylated with 5 units of polynucleotide kinase in 10 μl reaction mixtures containing 50 mM Tris-HCl (pH 7.4), 10 mM MgCl$_2$, 0.1 mM EDTA, 5 mM DTT, 0.1 mM Spermidine-HCl 12.5M ATP, and 37.5 μC [$\gamma$-32p] ATP (carrier-free) at 37° C. for 30 minutes. The reactions were terminated by heating at 65° C. for 5 min. followed by the addition of 5 μl of 10 mg/ml tRNA, and 190 μl of 5M ammonium acetate. The nucleic acids were ethanol precipitated, resuspended in 200 μl of 0.3M sodium acetate, ethanol precipitated again, dried under a vacuum and resuspended in 10 μl of 1 mM Tris(pH 7.4), 0.1 mM EDTA (0.1×TE).

The two halves of the GRF gene (RF-N and RF-C) were assembled separately following the schemes outlined in FIG. 15. 8 pmoles each of the phosphorylated oligonucleotides were ligated with 4 units of T4 DNA ligase in reaction mixtures containing 50 mM Tris(pH 7.4), 10 mM MgCl$_2$, 10 mM DTT, and 0.3 mM ATP at 15° C. for 30 to 60 minutes. At the end of the sequential ligations, an additional 200 units of ligase was added and incubation was continued at 4° C. for 2 days. The ligation reactions were terminated by heating at 65° C. for 5 min, then chilled on ice. The ligated molecules were digested with PstI and EcoRI, ethanol precipitated, and separated by electrophoresis on a 8% polyacrylamide gel. The 80 bp product comprising the N-terminal portion of the GRF gene, and the 70 bp product comprising the C-terminal portion were identified following autoradiography, recovered from the gel, ethanol precipitated twice, dried, and resuspended in 10 μl of 0.1×TE.

EXAMPLE 10

For direct expression of the GRF gene product in *E. coli*, the EcoRI-Sal I fragment containing the GRF gene is inserted into the expression vector pRC23 which has been digested with EcoRI and Sal I. pRC23 is a derivative of pBR322 which contains the bacteriophage lambda P$_L$ promoter and a synthetic Shine-Delgarno (SD) sequence adjacent to the EcoRI site (see FIG. 1). Joining the GRF sequence at this EcoRI site creates a very favorable ribosome-binding site for efficient translation initiation. Transcription initiation from the strong P$_L$ promoter is conveniently and efficiently controlled by the temperature-sensitive cI repressor encoded by the low-copy number plasmid pRK248 cIts.

Specific procedures for constructing the aforesaid recombinant plasmid using the monomer construction from Example 9 are set forth below:

3 μl of the purified RF-N and RF-C fragments were ligated together in a 10 μl reaction mixture as described in Example 9 with 200 units at T4 DNA ligase at 15° C. for 15 hrs. The reaction was terminated by heating at 65° C. for 5 min. then chilled on ice. The ligated molecules were digested with EcoRI and Sal I, and then ligated as before to 200 ng of the vector pRC23 (which has also been digested with EcoRI and Sal I). The ligation mixture was used to transform strain RRI (pRK248cIts) following standard procedures. Transformants were selected on media containing ampicillin (50 μg/ml). Approximately 200 transformants were obtained. Plasmid DNA was isolated from 10 of the transformants and analyzed by digestion with Ava I (which cuts once within the GRF gene and once in pRC23). 7 out of the 10 showed the expected restriction pattern. Maxam-Gilbert nucleotide sequence analysis of one of these confirmed the expected sequence of the entire GRF gene as shown in FIG. 2. This transformant was designated RRi(pRK248cIts, pRC23/GRF-1).

To test for expression of the cloned synthetic GRF gene, two approaches were taken: (1) to analyze the cell-free translation products encoded by pRC23/GRF-1, and (2) to assay lysates of induced cells containing pRC23/GRF-1 for GRF bio-activity. The details of these experiments are described below.

(1) Purified pRC23/GRF-1 DNA (along with control DNA) was added to a coupled in vitro transcription-translation system [Kung, et al. Arch. Biochem. Biophys. 195–396 (1979)] containing $^{35}$S-methionine and the resulting products were analyzed by SDS-polyacrylamide gel electrophoresis followed by fluorography. The results indicated that pRC23/GRF-1 directs the synthesis of a polypeptide of 5–6 kilodaltons (authentic GRF-44 is about 5.3 Kd) that is not produced by the control pRC23 DNA. Parallel reactions (carried out with unlabeled methione) were tested for bioactivity as described below.

(2) Strain RRI (pRK248cIts, pRC23/GRF/1) was grown in M9-glucose media at 30° C. to about 2×10$^8$ cells/ml, then induced at 42° C. for 2 hrs. 1 ml samples were taken and the cells were collected by centrifugation. The cells were resuspended in 50 μl of 50 mM Tris(pH 7.4), 10% sucrose and quickly frozen in a dry ice/ethanol bath. The cells were thawed and kept at 0°–4° C. 5 μl of lysis mix (1 vol of 5 m NaCl, 1 vol 0.5M EDTA, 1 vol 1M Spermidine-HCl, and 2 vol 5 mg/ml lysozyme) was added, and after 30 min on ice, the mixture was incubated at 37° C. for 2 min. Lysis was complete after an additional cycle of freezing and thawing. Cell debris was removed by centrifugation and lysates were quickly frozen in a dry ice/ethanol bath. The lysates together with the cell-free translation products described above were assayed for GRF biological activity as described in Brazeau, et al. Regul. Peptides 1, 255 (1981). The results shown in Table 2 demonstrate that the synthetic gene for GRF cloned in the expression vector pRC23 directs the synthesis of biologically active GRF polypeptide.

TABLE 2

| Sample Number | Plasmid | GRF Activity Percent of Control |
|---|---|---|
| 1 | Control (media only) | 100 |
| 2 | Control + 25 fmoles of GRF-NH$_2$ (44) | 320 |
| 3 | pRC23 + 25 fmoles of GRF-NH$_2$ (44) | 109* |
| 4 | pRC23/IGN-γ | 65 |
| 5 | pRC23/GRF-1 | 96 |
| 6 | pRC23/GRF-9 | 97 |
| 7 | pRC23 | 47 |
| 8 | pRC23/IFN-γ | 59 |
| 9 | pRC23/GRF-9 | 104 |

Purification of the GRF polypeptide from the lysate can be accomplished using chromatography procedures well known in the art. Such procedures include affinity chromatography employing supported GRF polyclonal or monoclonal antibody, column chromatography or preferably one or more reverse phase HPLC procedures. Combinations of such chromatography methods may also be employed. In this manner recombinant GRF-OH(44) is obtained in homogeneous form suitable for therapeutic use.

EXAMPLE 11

GRF-OH(37)Gene: DNA fragments Nos. 1 to 13 used for the construction of GRF gene are also used for the gene of GRF-OH(37). Additionally three new fragments 14', 15' and 16' are synthesized by analogy to Examples phosphite solid support methodology and ligated to the partial structural gene of GRF (containing up to fragment No. 13) to produce the structural gene for GRF-37 as shown graphically in FIG. 13.

EXAMPLE 12

GRF-OH(40): The partial structural gene for GRF (containing up to fragment No. 13) is ligated to the unit obtained from three new DNA fragments Nos. 14", 15" and 16" which are synthesized by the triester solid support methodology in analogy to Examples, to produce the structural gene for GRF-OH(40).

The cloning and expression of the genes for GRF-OH(37) and GRF-OH(40) may be carried out by the same procedures described above for the gene for GRF-OH(44).

We claim:

1. A recombinant double-stranded DNA molecule having cohesive termini with each terminus comprising a single strand of a double stranded restriction endonuclease recognition site and between the termini, a structural gene coding for human GRF-OH (1-44) or a biologically active fragment of human GRF of at least 37 amino acids that stimulates secretion of human growth hormone releasing factor.

2. A polydeoxyribonucleotide according to claim 1 wherein the form of GRF is GRF-OH(44).

3. A polydeoxyribonucleotide according to claim 1 wherein said GRF form is GRF-OH(40).

4. A polydeoxyribonucleotide according to claim 1 wherein said GRF form is GRF-OH(37).

5. A polydeoxyribonucleotide according to claim 1 wherein the opposite termini each comprise different restriction endonuclease recognition sites.

6. A polydeoxyribonucleotide according to claim 5 wherein the termini coding for the amino terminal of said GRF has an EcoR I recognition site and the termini at the end coding for the carboxy terminus of GRF has a Sal recognition site.

7. A recombinant DNA sequence coding for human GRF-OH (1-44) or a biologically active fragment of human GRF of at least 37 amino acids that stimulates secretion of human growth hormone releasing factor operably linked with a DNA sequence capable of effecting microbial expression of said human GRF or said biologically active fragment.

8. A recombinant DNA microbial expression vehicle comprising promoter and operator DNA sequences and a DNA sequence coding for human GRF-OH (1-44) or a biologically active fragment of human GRF of at least 37 amino acids that stimulates the secretion of human growth hormone releasing factor, said replicable expression vehicle capable, in a transformant microorganism, of expressing said human GRF or said biologically active fragment.

9. The expression vehicle of claim 8 comprising a DNA sequence, said sequence comprising a promoter and operator derived from bacteriophage lambda, a hybrid ribosome binding site and DNA coding for a form of GRF selected from the group consisting of GRF-OH(44), GRF-OH(40) and GRF-OH(37).

10. The expression vehicle of claim 9 wherein the promoter and operator are P$_L$ and O$_L$.

11. The expression vehicle of claim 9 comprising pRC 23/EcoR I-Sal I into which has been cloned a structural gene for a form of GRF selected from the group consisting of GRF-OH(44), GRF-OH(40) and GRF-OH(37).

12. The expression vehicle of claim 11 wherein said form of GRF is GRF-OH(44).

13. The expression vehicle of claim 11 wherein said form of GRF is GRF-OH(40).

14. The expression vehicle of claim 11 wherein said form of GRF is GRF-OH(37).

15. A microorganism transformed with the expression vehicle of claim 9.

16. The microorganism according to claim 15 obtained by transforming an E. coli strain.

17. A transformed E. coli strain of claim 16 obtained by transforming E. coli with an expression of claim 12.

18. A transformed E. coli strain obtained by transforming E. coli with the expression vehicle of claim 13.

19. A transformed E. coli strain obtained by transforming E. coli with the expression vehicle of claim 14.

20. A method for the production of recombinant GRF comprising growing the microorganism of claim 15, inducing expression of the recombinant gene, lysing the microorganisms upon completion of the induction period and separating said GRF from the cellular constituents of said microorganism.

21. The method of claim 20 wherein said microorganism is grown at a temperature in the range of about 30° to 36° C. and gene expression is induced by raising the temperature to about 42° C.

22. The method of claim 21 wherein said GRF is GRF-OH(44).

23. The method of claim 21 wherein said GRF is GRF-OH(40).

24. The method of claim 21 wherein said GRF is GRF-OH(37).

25. The structural gene coding for GRF-OH(44) consisting of the nucleotide sequence set forth in FIG. 2.

Figure 14:
FIG. 14. Sequences for substitution oligonucleotide fragments 14", 15" and 16" and a partial construction of a gene segment (ligation point indicated by arrow) containing these fragments, which unit can be ligated to gene segment 1-13 to form a structural gene for production of GRF-OH(40) is shown.

26. A structural gene coding for GRF-OH(40) consisting of the nucleotide sequence obtained by ligating the gene segment set forth in FIG. 14 formed from fragment 14″, 15″ and 16″ with gene fragments 1–13 of FIG. 4.

27. A structural gene coding for GRF-OH(37) consisting of the nucleotide sequence obtained by ligating the gene segment set forth in FIG. 13 formed from fragments 14′, 15′ and 16′ with gene fragments 1–13 of FIG. 4.

* * * * *

UNITED STATES PATENT AND TRADEMARK OFFICE
CERTIFICATE OF CORRECTION

PATENT NO. : 4,728,609
DATED : March 1, 1988
INVENTOR(S) : Bhatt et al.

It is certified that error appears in the above—identified patent and that said Letters Patent is hereby corrected as shown below:

In the specification on the bottom of page 1 wherin it says "THE TRANSLATED SEQUENCE IS" under positions 33-35 of the DNA sequence which is AAC:
delete "AEN" and insert therefor --Asn--.

In the specification on page 3, figure 2 wherein it says "THE TRANSLATED SEQUENCE IS" under positions 33-35 of the DNA sequence which is AAC:
delete "AEN" and insert therefor --Asn--.

In Claim 1, line 56: after hormone delete "releasing factor" and insert therefor --.--

In Claim 7, line 6: after growth hormone delete "releasing factor".

In Claim 8, line 15: after growth hormone delete "releasing factor"

Signed and Sealed this

First Day of January, 1991

Attest:

HARRY F. MANBECK, JR.

*Attesting Officer*     *Commissioner of Patents and Trademarks*